(12) United States Patent
Krumme

(10) Patent No.: US 9,211,991 B2
(45) Date of Patent: Dec. 15, 2015

(54) PACKAGING FOR ACTIVE SUBSTANCE-CONTAINING FILMS AND METHOD FOR PRODUCING THEM

(75) Inventor: Markus Krumme, Allschwil (CH)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 306 days.

(21) Appl. No.: 12/310,829

(22) PCT Filed: Sep. 6, 2007

(86) PCT No.: PCT/EP2007/007333
§ 371 (c)(1),
(2), (4) Date: Jul. 27, 2009

(87) PCT Pub. No.: WO2008/028560
PCT Pub. Date: Mar. 13, 2008

(65) Prior Publication Data
US 2009/0283440 A1 Nov. 19, 2009

(30) Foreign Application Priority Data
Sep. 7, 2006 (DE) .......................... 10 2006 041 921

(51) Int. Cl.
| B65D 83/04 | (2006.01) |
| B65D 85/42 | (2006.01) |
| B65D 75/58 | (2006.01) |
| A61F 13/00 | (2006.01) |
| A61J 3/07 | (2006.01) |

(52) U.S. Cl.
CPC ... *B65D 75/5855* (2013.01); *A61F 2013/00646* (2013.01); *A61J 3/078* (2013.01); *B65D 2215/04* (2013.01); *Y10T 428/13* (2015.01)

(58) Field of Classification Search
CPC ..................................................... B65D 75/327
USPC .............. 206/534.1, 538, 528, 532, 484, 529, 206/534.2
See application file for complete search history.

(56) References Cited

U.S. PATENT DOCUMENTS

| 3,924,746 A | 12/1975 | Haines |
| 3,933,245 A | 1/1976 | Mullen |
| 3,941,248 A * | 3/1976 | Moser et al. ................... 206/531 |
| 5,046,618 A * | 9/1991 | Wood ............................. 206/532 |
| 6,036,016 A * | 3/2000 | Arnold .......................... 206/532 |

(Continued)

FOREIGN PATENT DOCUMENTS

| DE | 23 22 055 | 1/1975 |
| DE | 19800682 | 7/1999 |

(Continued)

*Primary Examiner* — Luan K Bui
*Assistant Examiner* — Rafael Ortiz
(74) *Attorney, Agent, or Firm* — R. S. Lombard

(57) ABSTRACT

A packaging for active substance-containing films. The packaging comprises a carrier layer and a covering layer connected releasably to the latter, has in a paired arrangement two opposite surface regions which are separated from one another by a web and within which the covering layer is not connected to the carrier layer. Two spaces are formed, separate from one another and enclosed on all sides, for receiving the films in pairs. Within the web, a further surface region is present, in which the carrier layer is not connected to the covering layer, with the result that a cavity enclosed on all sides is formed. At least one perforation line is present within the web.

1 Claim, 3 Drawing Sheets

(56) References Cited

U.S. PATENT DOCUMENTS

| | | | |
|---|---|---|---|
| 6,155,423 A * | 12/2000 | Katzner et al. | 206/531 |
| 6,244,442 B1 * | 6/2001 | Inoue et al. | 206/531 |
| 6,655,112 B1 | 12/2003 | Cremer et al. | |
| 6,974,032 B2 * | 12/2005 | Intini | 206/532 |
| 7,121,410 B2 * | 10/2006 | Rohrmus et al. | 206/531 |
| 7,293,653 B2 | 11/2007 | Von Falkenhausen | |
| 2005/0258065 A1 | 11/2005 | Stroppolo et al. | |
| 2005/0269236 A1 * | 12/2005 | Rohrmus et al. | 206/531 |
| 2006/0054529 A1 * | 3/2006 | Intini | 206/532 |
| 2007/0012592 A1 * | 1/2007 | Bertsch et al. | 206/531 |
| 2008/0105582 A1 | 5/2008 | Ludwig et al. | |
| 2008/0190809 A1 * | 8/2008 | Simon et al. | 206/532 |

FOREIGN PATENT DOCUMENTS

| | | |
|---|---|---|
| DE | 101 02 818 | 8/2002 |
| DE | 203 20 948 | 7/2005 |
| DE | 10 2004 047445 | 4/2006 |
| DE | 102004047447 | 4/2006 |
| EP | 1477425 | 11/2004 |
| EP | 1602593 | 12/2005 |
| WO | WO 82/03372 | 10/1982 |
| WO | WO 99/54231 | 10/1999 |

\* cited by examiner

PACKAGING FOR ACTIVE SUBSTANCE-CONTAINING FILMS AND METHOD FOR PRODUCING THEM

CROSS-REFERENCE TO RELATED APPLICATIONS

This application is a National Stage application of International Application No. PCT/EP2007/007333, filed on Sep. 6, 2007, which claims priority of German application number 10 2006 041 921.9, filed on Sep. 7, 2006, both of which are incorporated herein by reference in their entireties.

BACKGROUND OF THE INVENTION

1. Field of the Invention

The invention relates to packagings for active substance-containing films, in particular for films having pharmaceutical active substances. It relates, furthermore, to the use of these packagings for the packaging of active substance-containing films, and to production methods, by means of which the packagings according to the invention can be obtained. The packagings according to the invention are suitable particularly for the child-proof packaging of active substance-containing films.

2. Description of the Prior Art

In drug therapy, in addition to the known forms of administration, such as tablets, capsules, etc., active substance-containing films, what are known as "wafers", are used for administering drugs, above all for oral administration. These are thin wafers or strips consisting of an active substance-containing film, these wafers or strips being co-ordinated in their thickness and dimensions with the active substance quantity to be dispensed. A wafer is generally flexible, soft, of low weight and tearable. The overall thickness of a film-like drug of this type may be 5 μm to 5 mm, usually 50 μm to 1 mm. The surface shape may be of round, oval, triangular or quadrangular or even polygonal configuration or have a shape rounded in any desired way. Drugs of all classes may be considered as active substances, for example analgesics or psychopharmaceuticals or else nicotine for curing the smoking habit. The active substance contained in the active substance-containing film, after being administered to a patient, is released from the film and can thereafter be resorbed.

On account of the active substance content of the active substance-containing films, it is desirable or even absolutely necessary to package these in such a way that they cannot be extracted and taken or swallowed by unauthorized persons, in particular by children. The opening operation should at least be impeded or delayed. On the other hand, such a child-proof packaging should nevertheless be capable of being opened by adults without much effort and without the aid of implements.

In an already known product (THERAFLU®, Novartis AG), an active substance-containing film strip is enclosed between a carrier layer and a covering layer which are connected to one another by means of sealing seams. Such a packaging (90) is illustrated diagrammatically in a top view in FIG. 1. The two packaging material sheets (carrier layer and covering layer) are sealed to one another in the region of the hatched areas. The packaging has an outer sealing margin (92) and also a web (95) which subdivides the inner space of the bag thus formed into two compartments (93, 94). The first space (93) contains the packaged active substance-containing film strip (91), and the second space (94) is empty and serves for forming a child-proof tear-open aid. For this purpose, the packaging is provided, in a region of the sealed outer margin, with a perforation or punching (96) which is spaced apart from the outer margin. To open the packaging, the latter has to be bent along the line (y), with the result that it becomes possible to tear into the packaging along the line (x) which runs through the surface region of the second space (94). By the tearing in or tearing off, freely accessible edges of the carrier layer and covering layer are formed, which serve as a grasping aid and which make it possible to pull off the covering layer from the carrier layer, with the result that the packaging contents (91) become accessible. Impeding the opening operation as a consequence of the construction substantially contributes to making the packaging child-proof.

However, the known packaging described above also has considerable disadvantages. Since the area required for forming the tear-open aid (94) is relatively large and amounts to approximately 30% of the area of the compartment (93) intended for receiving the film strip, the outlay in terms of material is too high in relation to the size of the film strip to be packaged and increases the production costs. The useful area (93) for enclosing the packaged contents is too low in relation to the overall area of the packaging and is approximately 40%. This means not only an increased consumption of material in production, but also an increased space requirement for storage.

In addition, in the packaging described above, the sealing seams, by means of which the carrier layer and covering layer are connected releasably to one another, occupy a considerable fraction of the overall area of the packaging, to be precise approximately 30%. The production speed consequently has to be reduced correspondingly, thus resulting, in turn, in an increase in the production costs.

SUMMARY OF THE PRESENT INVENTION

The object of the present invention, therefore, was to provide a packaging for active substance-containing films and a production method suitable for this purpose, while at the same time this packaging is to allow a child-proof packaging of active substance-containing films, but with the above-mentioned disadvantages being avoided or reduced. In particular, the object was to reduce the use of material, to increase the production speed and to allow a better utilization of the area of the packaging.

This object is achieved, according to the invention, by means of a packaging for active substance-containing films, which has a carrier layer and a covering layer connected releasably to the latter, the packaging having two opposite or opposing surface regions in a paired arrangement which are separated from one another by a web and within which the covering layer is not connected to the carrier layer, with the result that two spaces, separate from one another and enclosed on all sides, for receiving said films in pairs are formed;

within said web, a further surface region being present, in which the carrier layer is not connected to the covering layer, with the result that a cavity enclosed on all sides is formed;

at least one perforation line being present within the web.

Owing to the paired arrangement of two opposite spaces for receiving the active substance-containing film strips, an optimal utilization of the overall area of the packaging and, consequently, a reduction in the consumption of material are brought about. By the further surface region which forms the tear-open aid being arranged in the region of the web of the double packaging, the area required for this purpose is reduced in relation to the surface regions which are intended for accommodating the packaged contents. Furthermore, the arrangement according to the invention of said surface regions makes it possible for the sealing seams which connect the covering layer to the carrier layer in the region of the web to have a substantially narrower form than the peripheral sealing seam at the outer margin of the packaging. Overall, a reduction in the surfaces to be connected by sealing is thereby achieved, so that higher production speeds become possible. In addition, the packaging according to the invention also has features which, in a similar way to the known product described above, allow the child-proof packaging of active substance-containing products.

By active substance-containing films being packaged in pairs, double the number of active substance-containing films can be packaged in a predetermined duration of the sealing operation. This results in an additional increase in the production speed.

The packagings according to the invention are suitable particularly for the paired packaging of those active substance-containing films which, because of the type or dose of active substance or active substances contained in them, are, as a rule, extracted from the packaging simultaneously or in succession at a short time interval. This situation often arises, for example, in the case of analgesics when, because of the intensity of the pain, it is necessary to administer a double dose. Moreover, the packagings according to the invention may be used, in particular, for the paired packaging of films which contain different active substances and which are extracted in each case in pairs from the packaging for the purpose of administering an active substance combination.

Packaging materials consisting of paper, cardboard, plastic films (for example, polyethylene, polyethyleneterephthalate, polypropylene, polystyrene, cellophane, polyamides, polycarbonates, ethylene vinylacetate copolymer), and metal foils (for example, aluminum foil) and also composite materials composed of said materials may be considered for producing the carrier layer and the covering layer. A further preferred film material is BAREX® (BP Chemicals), a copolymer of acrylonitrile and butadiene. On account of its good barrier properties and chemical resistance, it is suitable particularly for the packaging of drugs having a content of aggressive and/or volatile active substances, for example nicotine.

In order to rule out an unauthorized or inadvertent destruction of the packaging by tearing apart, pointed articles, etc., it is necessary for each of the two packaging material components (carrier layer, covering layer) to have a sufficient tear strength (for example, according to DIN 53455 or EN-ISO 527). Materials suitable for this purpose are known to a person skilled in the art. The thickness of the carrier layer and of the covering layer is preferably in the range of 0.01 to 2 mm, in particular of 0.05 to 0.5 mm. In a preferred embodiment of the invention, the carrier layer of the packaging has a higher thickness than the covering layer.

The carrier layer and covering layer may be produced from the same materials or from different types of materials. Preferably, at least one of the two packaging material fractions (carrier layer, covering layer) consists of transparent material (for example, transparent plastic film).

Furthermore, the invention embraces embodiments in which one packaging material fraction or both packaging material fractions is or are colored identically or differently in a coloring which in each case may be transparent or opaque.

For example the carrier sheet may be produced from a non-transparent composite material consisting of paper (or cardboard) with plastics (for example, with polyethylene- or polyethyleneterephthalate-coated papers), and the covering layer may be produced from a transparent colorless or colored plastic film. To reduce permeability to air, to light and to water vapor, it is advantageous if at least one surface of the carrier layer and/or of the covering layer is metallized (for example, coated with aluminum).

The packaging according to the invention can be produced in the most diverse possible geometric shapes (for example, rectangle, trapezium, ellipse) and in different dimensions. The surface extent is generally dependent on the size of the packaged contents (for example, wafers) and is usually in the range of 10 to 100 $cm^2$. The size of the first surface region for receiving the packaged contents can likewise be varied within wide ranges, depending on the surface extent of the articles to be packaged. The carrier sheet and covering layer may have an identical shape and size; however, embodiments are also provided in which the covering layer has a smaller size than the carrier layer and/or a geometric shape deviating from the carrier layer.

The carrier layer is connected releasably to the covering layer, specifically such that the covering layer can be pulled off from the carrier layer by means of finger force and without the aid of implements, as is known from other peelable packagings.

The releasable connection between the covering layer and carrier layer is preferably made by sealing or welding; suitable means and methods for generating sealing seams or sealing surfaces are known to a person skilled in the art. The seal serves as a diffusion and permeation barrier and is generally impermeable to active substances and atmospheric humidity. Both hot-sealing methods and cold-sealing methods may be considered. The material used for sealing layers may be, for example, hot-melt adhesives (hotmelts; for example based on polyethylene LD), sealing lacquers, sealing dispersions or adhesives.

The releasable connection is preferably made by hot sealing at temperatures in the range of between 50° C. and 200° C., in particular 50 to 90° C., using hot melts.

The sealing seams or sealing surfaces preferably have a strength (=sealing strength) in the range of 1 N/15 mm to 50 N/15 mm, preferably 2 N/15 mm to 20 N/15 mm.

The carrier layer and covering layer are preferably connected to one another over the entire area, with the exception of said surface regions. In the region of the web, the two packaging material sheets (carrier layer and covering layer) are sealed to one another, with the exception of that region which forms the tear-open aid. The web runs essentially perpendicularly with respect to the longitudinal direction of the packaging.

As mentioned, the type of design according to the invention makes it possible to utilize the overall area of the packaging in a particularly beneficial way. According to a preferred embodiment of the invention, said surface regions are selected such that the sum of the areas of the two opposite surface regions which form the spaces for receiving said films corresponds to at least 50%, preferably at least 60%, of the overall area of the packaging. Furthermore, it is preferable that the area of said further surface region amounts to no more than 50%, preferably no more than 20%, particularly preferably no more than 15%, of the sum of the areas of the two opposite surface regions which form the spaces for receiving said films.

The two opposite surface regions which are arranged in pairs and which form the spaces for receiving said films preferably have the same size and the same geometric shape. For specific applications, however, it may be advantageous to configure these two surface regions differently.

With a view to as efficient a manufacture as possible, it is particularly advantageous if the two opposite surface regions which form the spaces for receiving said films have the same size and the same geometric shape and are arranged symmetrically with respect to the longitudinal direction of the packaging, and if the width of the web located between the two surface regions corresponds to double the width of the margin which runs between an end-face outer margin of the packaging and the contiguous surface region which is intended for receiving said film. The result of this is that, during manufacture, a virtually uniform spacing between the respectively adjacent active substance-containing films (with respect to the longitudinal direction of the packagings) can be maintained. As a result, the production process is substantially simpler, and higher process speeds become possible. Moreover, a substantially uniform product spread in the longitudinal direction is thereby possible. If required, the spacing between the respectively adjacent active substance-containing films may also be set exactly uniformly, thus resulting in a maximum manufacturing speed.

Furthermore, said surface regions are preferably so dimensioned and arranged in such a way that the sum of the surface regions in which the covering layer is connected to the carrier layer amounts to no more than 25%, preferably no more than 20%. The time required for the sealing operation can thus be reduced. The product stability of the packaged films is ensured by the sealing seam running along the outer margin of the packaging. The width of said sealing seam preferably amounts to at least 3 mm, in particular at least 5 mm. For the sealing margins which run in the region of the web and which separate the first or the second surface region from said further surface region, a width of 1.5 to 2 mm is sufficient for ensuring that the packaged contents are protected.

According to a preferred embodiment, the packaging according to the invention is constructed in such a way that, between each of the two surface regions, which form the spaces, enclosed on all sides, for receiving said films, and the respectively adjacent outer margin of the packaging, there is a region within which the carrier layer is connected to the covering layer and which has a width of 3 to 7 mm, preferably 4-5 mm.

To form a tear-open aid, in the packagings according to the invention there is, within said web, a further surface region in which the carrier layer is not connected to the covering layer, with the result that a cavity enclosed on all sides is formed. The latter serves merely for forming a grasping and tear-open aid and is not intended for the reception of active substance-containing films.

Said further surface region is preferably of elongate shape. According to a preferred embodiment, said further surface region is provided with a wavy or sawtooth-shaped contour, thus making the peeling or pulling-off operation easier. This is advantageous particularly when the grasping aid formed after the tearing of the perforation is relatively short.

As mentioned, at least one perforation line is present within the web. This perforation line is preferably designed such that it runs in the direction of said further surface region. By tearing into the carrier layer and covering layer at the perforation line and by subsequently continuing to tear, said second surface region is divided approximately into two halves. Severing the two layers of the packaging gives rise to free edges which can serve as a tear-open aid, as described above. Thus, when the packaging is being torn into, a tear-open aid is generated for each of the two spaces in which the active substance-containing films are enclosed.

Said perforation line may be generated in a known way, for example by punching. In addition to such perforation lines, other types of weakening lines may also be considered, in so far as they make it possible to tear into the packaging. The perforation line is preferably designed such that the finger force required for severing can easily be applied by adult persons, but generally not by small children.

The child-proof facility is achieved in that, to open the packaging, at least three co-ordinated manual actions are required: (i) bending the packaging in the marginal region in order to make the perforation line accessible; (ii) tearing into and continuing to tear the perforation, and (iii) gripping the free edges thus generated, as a grasping aid (or grasping tab), and pulling the carrier layer and covering layer apart.

Structures particularly suitable for making it possible to tear into the element or elements of the packaging material are: straight cuts; serrated or wavy cuts; perforations, in particular perforations consisting of dots arranged one behind the other, and/or cuts; material clearances; punchings, in particular arrow-shaped, triangular or lozenge-shaped punchings; predetermined breaking points or embossed lines.

In order to make said operation of folding or bending the packaging easier, it is advantageous to provide the packaging with a folding line or bending line, for example by embossing or pinching. Methods suitable for this purpose are known to a person skilled in the art.

Said folding line or bending line is preferably arranged such that it runs in the longitudinal direction of the packaging and touches or intersects, for example at right angles, said perforation line. The tearing-in operation is thereby made considerably easier, without the child-proof facility of the packaging being impaired.

This is important particularly with regard to the intended use of the packaging by older persons, since, even in this case, it is necessary to ensure that the packaging can be opened without the aid of implements or other aids, and that opening is possible within a short time and without frustrating attempts.

The perforation line or perforation lines or at least one of the perforation lines is/are formed preferably both in the carrier layer and in the covering layer, in order to make simple and reliable tearing possible.

Regarding position of the perforation lines, it is preferable that the perforation line or perforation lines or at least one of the perforation lines is/are arranged in the region which is located between the outer margin of the packaging and said further surface region. In order to ensure the desired child-proof facility, the perforation line or perforation lines should preferably not reach as far as the outer margin of the packaging.

According to a preferred embodiment of the invention, there is provision for the perforation line or perforation lines or at least one of the perforation lines not to reach as far as said further surface region which is intended for forming the tear-open aid.

Alternatively, according to a further preferred embodiment of the invention, there is provision for the perforation line or perforation lines or at least one of the perforation lines to reach as far as said further surface region or to extend into this. Further, it may be advantageous to design the perforation line such that it runs completely through said further surface region, preferably centrally.

On account of the design features described above, the packaging according to the invention is suitable for the child-proof packaging of active substance-containing films. The invention therefore embraces child-proof non-reclosable packagings having the above-described features. In particular, the present invention embraces packagings of the above-described type, which are distinguished in that they are child-proof according to the standards of DIN EN 14375 and/or according to ASTM D3475-03a.

The packagings according to the invention are suitable for the packaging, in particular child-proof packaging, of active substance-containing films of the type described initially. Active substances which may be considered are, in addition to said pharmaceutical active substances, also cosmetic active substances, flavorings and aromatics, nutrients, vitamins, diagnostic reagents, toxins and active substances which are used in plant protection or pest control.

The invention provides, furthermore, a method for the packaging of active substance-containing films, the method having the following steps:

provision of or providing of a carrier layer;

positioning of two active substance-containing films in a paired arrangement on the carrier layer;

covering of the carrier layer and of the active substance-containing films located on it with a covering layer;

connection of the carrier layer and covering layer by means of a releasable connection, specifically in such a way that the two surface regions which enclose the active substance-containing films are surrounded completely by a marginal region in which the carrier layer is connected to the covering layer. As a result, two spaces, which are enclosed on all sides and contain the two films to be packaged, and also a web lying between these spaces, are formed. The connection of the carrier layer and covering layer takes place in such a way that the packaging has, in the region of the web present between said two surface regions, a further surface region in which the carrier layer is not connected to the covering layer;

generation of at least one perforation line within the web. This perforation line is preferably designed in such a way that it runs in the direction of said further surface region.

According to a preferred embodiment, the method is carried out in such a way that the two opposite surface regions which form the spaces for receiving said films have the same size and the same geometric shape and are arranged symmetrically. Furthermore, the web located between the two surface regions is designed in such a way that its width corresponds to double the width of that margin which runs between an end-face outer margin of the packaging and the contiguous surface region which is intended for receiving said film.

BRIEF DESCRIPTION OF THE DRAWINGS

The features, details and advantages of the invention are explained by way of example below by means of the embodiments illustrated diagrammatically in the drawings. The illustrations in the drawings do not necessarily reproduce the actual size proportions.

DETAILED DESCRIPTION OF THE PRESENT INVENTION

Figure 2A:
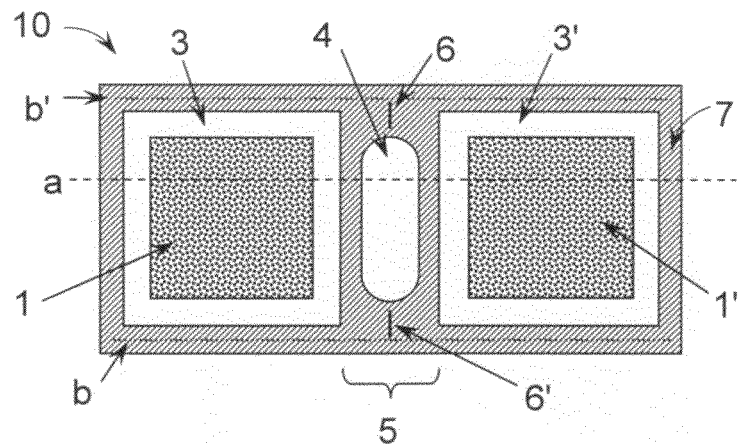
FIG. 2A is a top view of a packaging according to the invention.
Figure 2B:
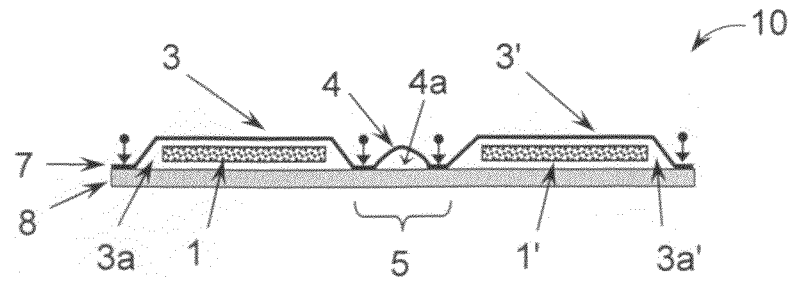
FIG. 2B is a cross-section view in the plane (a) of FIG. 2A.

FIG. 2A shows a packaging (10) having a rectangular horizontal projection, which is constructed from a covering layer (7) and a carrier layer lying beneath the latter and connected to the covering layer (see FIG. 2B). The covering layer is illustrated transparently in FIG. 2A.

The packaging has a first surface region (3) and a second surface region (3'), within which the covering layer is not connected to the carrier layer. Within the surface regions (3, 3'), are located the packaged active substance-containing films (1, 1'). The covering layer (7) has the same geometric shape and size as the carrier layer lying beneath it and is connected to the latter over the entire area and releasably, that is to say peelably (hatched regions), with the exception of the first and the second surface region (3, 3').

The two surface regions (3, 3') are surrounded completely by a margin in which the covering foil (7) is connected to the carrier layer. Between the first surface region (3) and the second surface region (3') is located a web (5), in the region of which the covering foil is likewise connected to the carrier layer. Within the web (5), and in each case spaced apart from the surface regions (3, 3'), a further surface region (4) is located, within which the covering foil (7) is not connected to the carrier foil and which serves for forming a grasping and tear-open aid.

In the region of the web (5), two weakening lines in the form of perforation lines (6, 6') are formed, specifically spaced apart from the outer margin and from the further surface region (4). The perforation lines run perpendicularly with respect to the longitudinal direction of the packaging (line a), in the same way as the elongate surface region (4), and are arranged centrally with respect to this surface region.

The packaging has, furthermore, a bending line (b) which runs in the longitudinal direction and which runs in a lateral marginal region and touches the perforation line (6').

A second bending line (b') may optionally be provided. After the outer margin of the packaging has been bent round along the bending line (b or b'), the packaging can be torn into along one of the perforation lines (6, 6'), and the covering foil and carrier foil are divided in the region of the surface region (4) into two halves of approximately equal size. The free edges, formed by the tear, of the covering layer and carrier layer can then be used as grasping and tear-open aids, in order to detach the two layers from one another and making it possible to extract the active substance-containing films (1, 1').

For example, the packaging shown in FIG. 2A has a length of 96 mm and a width of 42 mm. The sealing seam surrounding the first and the second surface region is 5 mm wide, so that each of these surface regions has a size of 32×32 mm. The active substance-containing films (1, 1') to be packaged have in this example a size of approximately 22×22 mm. The surface region (4) lying in the region of the web has, as regards its elongate shape, a width of 10 mm and is separated from the adjacent surface regions (3, 3') by a 5 mm wide sealing seam, so that the overall width of the web amounts to 20 mm in this example. When the packaging is being opened, a grasping aid with a length of approximately 5 to 5.5 mm (with respect to the longitudinal direction of the packaging) is formed from the surface region (4) for each of the two packaged films.

FIG. 2B shows a section in the plane (a) of FIG. 2A. The packaging is constructed from a carrier layer (8) and a covering layer (7). The two layers are connected releasably to one another in the regions designated by arrows. In the region of the surface regions (3, 3'), the two layers are not connected to one another and form spaces (3a, 3a') for receiving the active substance-containing films (1, 1'). In the region of the surface region (4), a cavity (4a) is formed by the layers not connected to one another.

Figure 1:
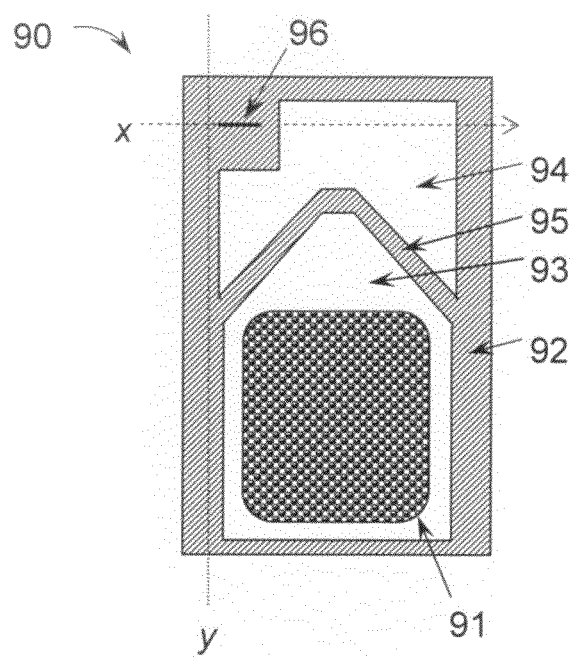
FIG. 1 is a top view of a prior art packaging.
Figure 3A:
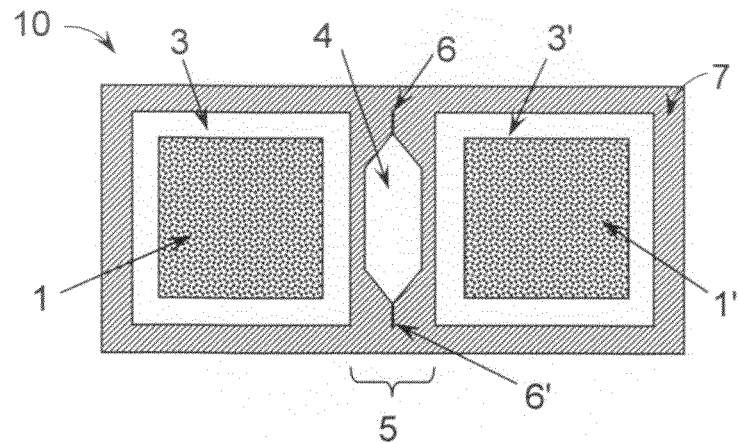
FIGS. 3A, 3B, 3C and 3D are tops views of further embodiments of the packaging according to the invention.

FIG. 3A shows a modification of the packaging shown in FIG. 1a, the further surface region (4) being in the shape of an elongate polygon, and the two opposite perforations (6, 6'), which run approximately perpendicularly with respect to the longitudinal direction of the packaging, reaching as far as this surface region (4).

Figure 3B:
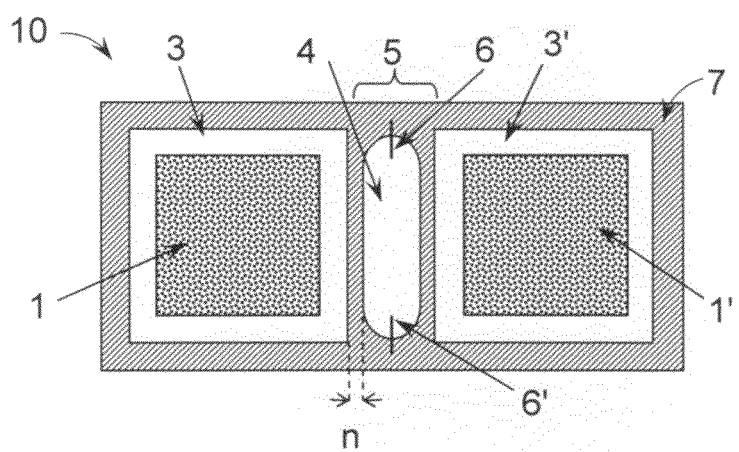

FIG. 3B shows a further modification of the packaging shown in FIG. 1A, the perforations (6, 6') being prolonged into the inner space of the further surface region (4).

The width (n) of the sealing seam which delimits the surface region (4) with respect to the surface regions (3, 3') may be smaller than the width of the sealing seams which close off the surface regions (3, 3') toward the outer margin of the packaging. Assuming the dimensions given by way of example in FIG. 2A, the width (n) may amount, for example, to 2 mm. This makes it possible to increase the width of the surface region (4) (with respect to its longitudinal direction) (for example, 25 mm), so that the grasping aids emanating from it are larger and can be gripped more readily.

Figure 3C:
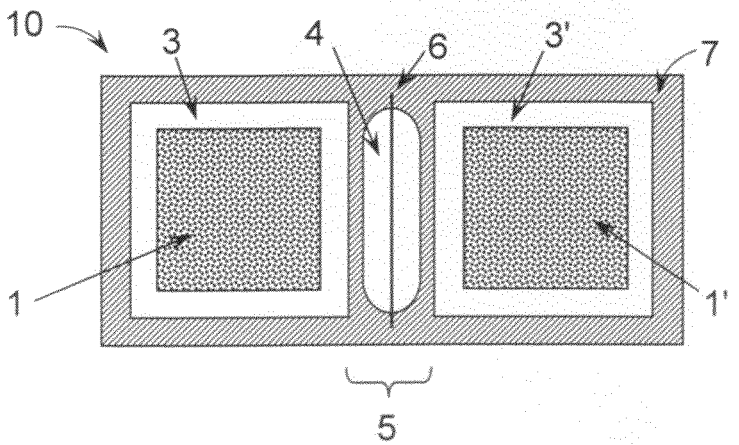

FIG. 3C shows a further modification of the packaging shown in FIG. 1A, the perforation line (6) running completely through the inner space of the further surface region (4).

Figure 3D:
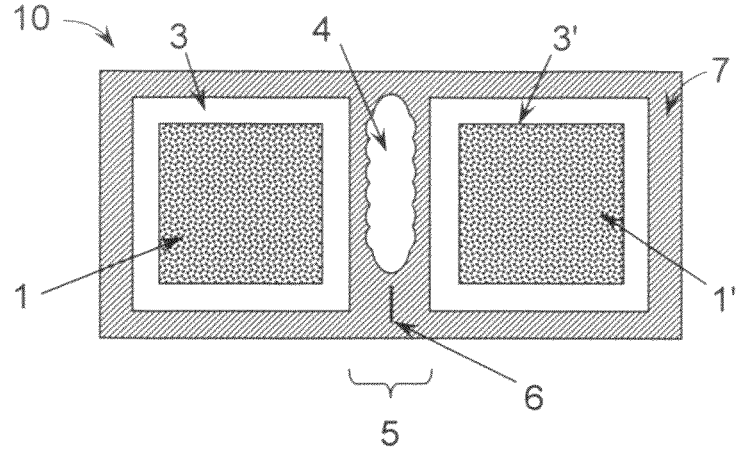

FIG. 3D shows a further modification of the packaging shown in FIG. 1A, the surface region (4) which lies in the region of the web (5) having a serrated or wavy contour. The perforation line (6) formed in the web region is located in the region between the outer edge of the packaging and the surface region (4).

Figure 4:
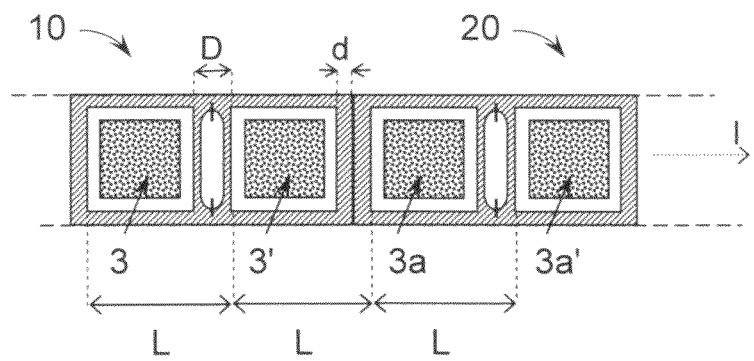
FIG. 4 is a top view of two packagings arranged one behind the other in the longitudinal direction, in the state during production.

FIG. 4 shows two successive packagings (10, 20) of the type shown in FIG. 3B during production. The two opposite surface regions which form the spaces for receiving the films (3, 3'; 3a, 3a') are essentially the same size with the same geometric shape and are arranged symmetrically with respect to the longitudinal direction (arrow 1). The web located between the two surface regions is designed in such a way that its width D corresponds to double the width d of the margin which runs between an end-face outer margin of the packaging and the contiguous surface region which is intended for receiving said film.

What is thereby achieved is that the active substance-containing films (3, 3'; 3a, 3a') can be packaged with a substantially uniform spacing L.

For example, each of the packagings shown in FIG. 4 has a length of 88 mm and a width of 42 mm. The sealing seam surrounding the first and the second surface region is 5 mm wide toward the outer margins of the packaging. The width of the sealing seam which in the region of the web (5) delimits the surface region (4) with respect to the surface regions (3, 3') is smaller than the width of the sealing seams which close off the surface regions (3, 3') toward the outer margin of the packaging and amounts to 1.5 to 2 mm. The elongate surface region (4) has a width of approximately 10 mm, so that, when the packaging is being opened, a grasping aid with a length of approximately 5 to 5.5 mm (with respect to the longitudinal direction of the packaging) is formed for each of the two packaged films. The surface region (4) is advantageously shaped as in FIG. 3D.

Each of the surface regions (3, 3') has a size of approximately 3×3 cm, and in this example the active substance-containing films (1, 1') to be packaged are a size of approximately 22×22 mm. In the described arrangement of the surface regions and of the sealing seams, the sealing seam width to be overcome by diffusion amounts to at least 5 mm between the inner spaces of the packaging and the surroundings, thus ensuring product stability as long as the packaging is unopened.

The invention advantageously makes it possible to reduce the material consumption and to increase the production speed in the production of child-proof packagings for active substance-containing films.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

The invention claimed is:

1. A packaging including active substance-containing films, said packaging comprising a carrier layer and a covering layer releasably connected to the carrier layer to form a releasable connection, and wherein the packaging comprises:

the covering layer having a rectangular outer margin around the perimeter of the packaging in surrounding direct contacting relationship with only two opposing surface regions in a paired arrangement and only a single web positioned between and for separating the two opposing surface regions, the single web in direct contacting relationship with the two opposing surface regions, the rectangular outer margin having a predetermined first width (d) which runs between the perimeter of the packaging and a contiguous one of the opposing surface regions, the single web in surrounding direct contacting relationship with only a single elongated further surface region wherein the carrier layer is not connected to the covering layer for forming a single cavity enclosed on all sides, the carrier layer releasably connected to the covering layer over the entirety of the rectangular outer margin without separation between the carrier layer and the cover layer, wherein the single web has a predetermined second width (D) between the two opposing surface regions which includes the width of the single elongated further surface region, the predetermined second width (D) of the single web corresponds to double the predetermined first width (d) of the outer margin, wherein the covering layer is not connected to the carrier layer within the two opposing surface regions, for forming two spaces, separate from one another and enclosed on all sides, each of the two spaces for receiving one of said active substance-containing films, the two opposing surface regions each have the same size and the same geometric shape as each other and are arranged symmetrically with respect to the longitudinal direction of the packaging;

at least one perforation line within the single web, the at least one perforation line arranged about perpendicular to the longitudinal direction of the rectangular outer margin of the packaging for dividing the single elongated further surface region into two halves for forming a tear-open aid within each half of the single elongated further surface region upon tearing along the at least one perforation line;

wherein said at least one perforation line or at least one of said at least one perforation line runs in the direction towards said further surface region; and, wherein said at least one perforation line or at least one of said at least one perforation line does not or do not reach as far as said further surface region.

* * * * *